United States Patent [19]

Shigemori et al.

[11] 4,369,647
[45] Jan. 25, 1983

[54] GAS LEAKAGE DETECTOR

[75] Inventors: Tesshi Shigemori, Nishinomiya; Yoshinao Nozawa, Suita; Teruhisa Kojima, Kawasaki; Satoshi Kitajima, Hiratsuka, all of Japan

[73] Assignee: New Cosmos Electric Company Limited, Osaka, Japan

[21] Appl. No.: 133,650

[22] Filed: Mar. 21, 1980

[51] Int. Cl.³ .................... G08B 17/10; G01N 31/00
[52] U.S. Cl. ........................... 73/27 R; 340/634
[58] Field of Search .................. 73/27; 340/632, 633, 340/634, 605

[56] References Cited

U.S. PATENT DOCUMENTS

| | | | |
|---|---|---|---|
| 2,582,859 | 1/1952 | Centofanti | 73/27 R |
| 3,311,455 | 3/1967 | Robinson | 73/27 R X |
| 3,370,457 | 2/1968 | Lemm | 73/27 R |
| 3,786,675 | 1/1974 | Delatorre et al. | 73/27 R |
| 3,950,739 | 4/1976 | Campman | |
| 4,166,380 | 9/1979 | Batz | 340/634 X |
| 4,219,806 | 8/1980 | Enemark | 73/27 R X |

FOREIGN PATENT DOCUMENTS

| | | |
|---|---|---|
| 54-139894 | 8/1979 | Japan . |
| 54-26888 | 9/1979 | Japan . |
| 54-34640 | 10/1979 | Japan . |
| 55-6864 | 2/1980 | Japan . |
| 1474700 | 5/1977 | United Kingdom . |

Primary Examiner—Edward R. Kazenske
Assistant Examiner—Joseph W. Roskos
Attorney, Agent, or Firm—Cushman, Darby & Cushman

[57] ABSTRACT

A gas leakage detector comprising a solid state gas sensor having a sintered metallic oxide block which changes thermal conductivity by chemical adsorption thereto and a wire for transforming thermal conductivity charges into an electric signal. A suction pump draws gas through a gas intake path to the gas sensor. A voltage-frequency converter generates a pulse frequency that is a function of the gas sensor voltage. An alarm indicator including sound and/or light is controlled to pulse by the output pulse of the voltage frequency converter.

32 Claims, 12 Drawing Figures

GAS LEAKAGE DETECTOR

BACKGROUND OF THE INVENTION

1. Field of the Invention

The present invention relates to a gas leakage detector.

More particularly the present invention concerns an improvement in a handy, portable and electronized gas leakage detector capable of detecting a very small amount of gas leakage and indicating detection by changing the manner of lighting an alarm lamp and/or sounding a buzzer.

2. Prior Art

Hitherto, several types of gas leakage detectors have been proposed, but most of them, for example a flame ionization detector, are large and of stationary types which can not be used handily, for example by a single hand. Therefore such apparatuses are not generally usable as portable apparatus by servicemen. Accordingly, a simple conventional method of a gas leakage detection has been using a detection liquid, such as a solution of soap to form bubbles at the gas leakage, but its limit of detection is about $5 \times 10^{-4}$ cc/sec.

Furthermore, even if the conventional apparatus is capable of measuring a small concentration of leaking gas, the conventional apparatus having an amperemeter or seven-element figure indicators to indicate the measured concentration is not actually useful in finding location of the gas leakage, since the operator of the apparatus has to carefully watch both the indicator and a position of the gas leakage to be detected. And accordingly, pulsated sound alarm or pulsated light alarm type solid state electronized gas detector has been proposed, but the conventional electronized detector still have two problems. First, they require a long warm-up time. Second, changes in pulsation frequency may go unobserved or produce erroneous indications, particularly at high and low frequencies.

SUMMARY OF THE INVENTION

Accordingly, the present invention provides an improved handy, portable and practically useful apparatus for detecting gas leakage.

The gas leakage detector of the present invention can detect gas leakages with a high sensitivity, a high stability and with a quick response time and easy operation.

DESCRIPTION OF PREFERRED EMBODIMENT

The present invention provides a novel gas leakage detector comprising:

a solid state gas sensor, having a sintered metallic oxide to change thermal conductivity by chemical adsorption thereto and a wire to transfer the change of the thermal conductivity to an electric signal, a gas intake path in which gas sensing part of said gas sensor is disposed, a suction pump connected to said gas intake path in a manner to take a gas to be detected into said gas intake path thereby to contact with said gas sensor, a variable frequency oscillator which changes frequency of its output pulse responding to input signal from the solid state gas sensor and an alarm indicator, sound or light of which is controlled to blink by the output pulse of said variable frequency oscillator.

A further feature of the present invention is that the pulsating sound and light is controlled in a manner such that the frequency of the pulse change between a predetermined lower limit which corresponds to a lower limit of the concentration of gas to be detected and a predetermined higher limit which corresponds to a higher limit of concentration of gas to be detected, and the time period of each block of light and sound is uniform irrespective of change of the pulsation frequency thereby making the light and sound continuous at the higher limit of concentration of gas.

A preferred embodiment of the gas leakage detector according to the present invention is now elucidated referring to the accompanying drawings.

Figure 1:
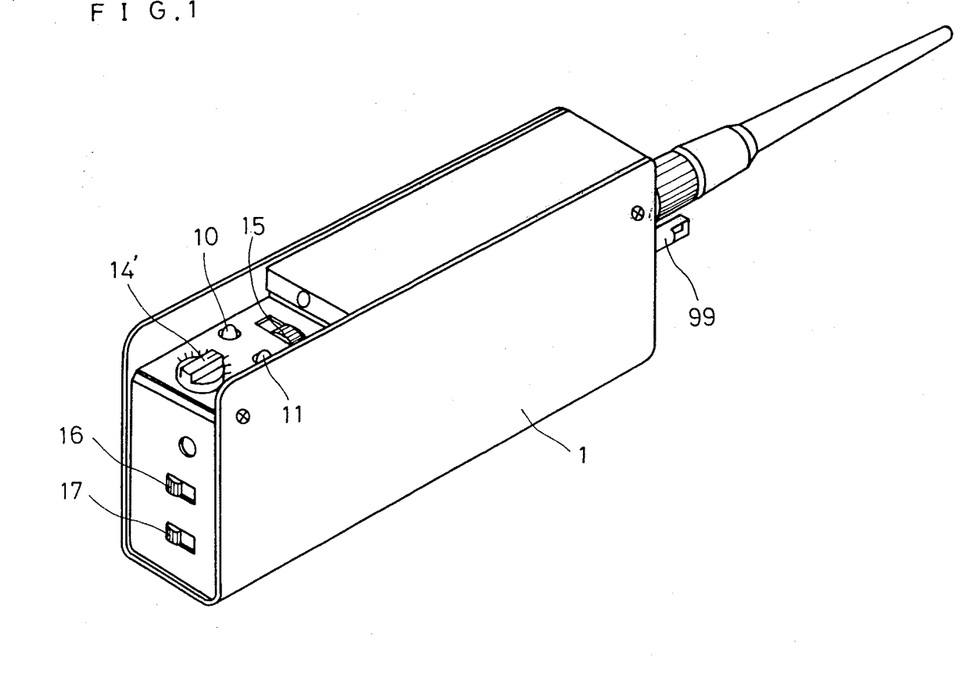
FIG. 1 is a perspective view showing overall appearance of a gas leakage detector embodying the present invention.
Figure 2:
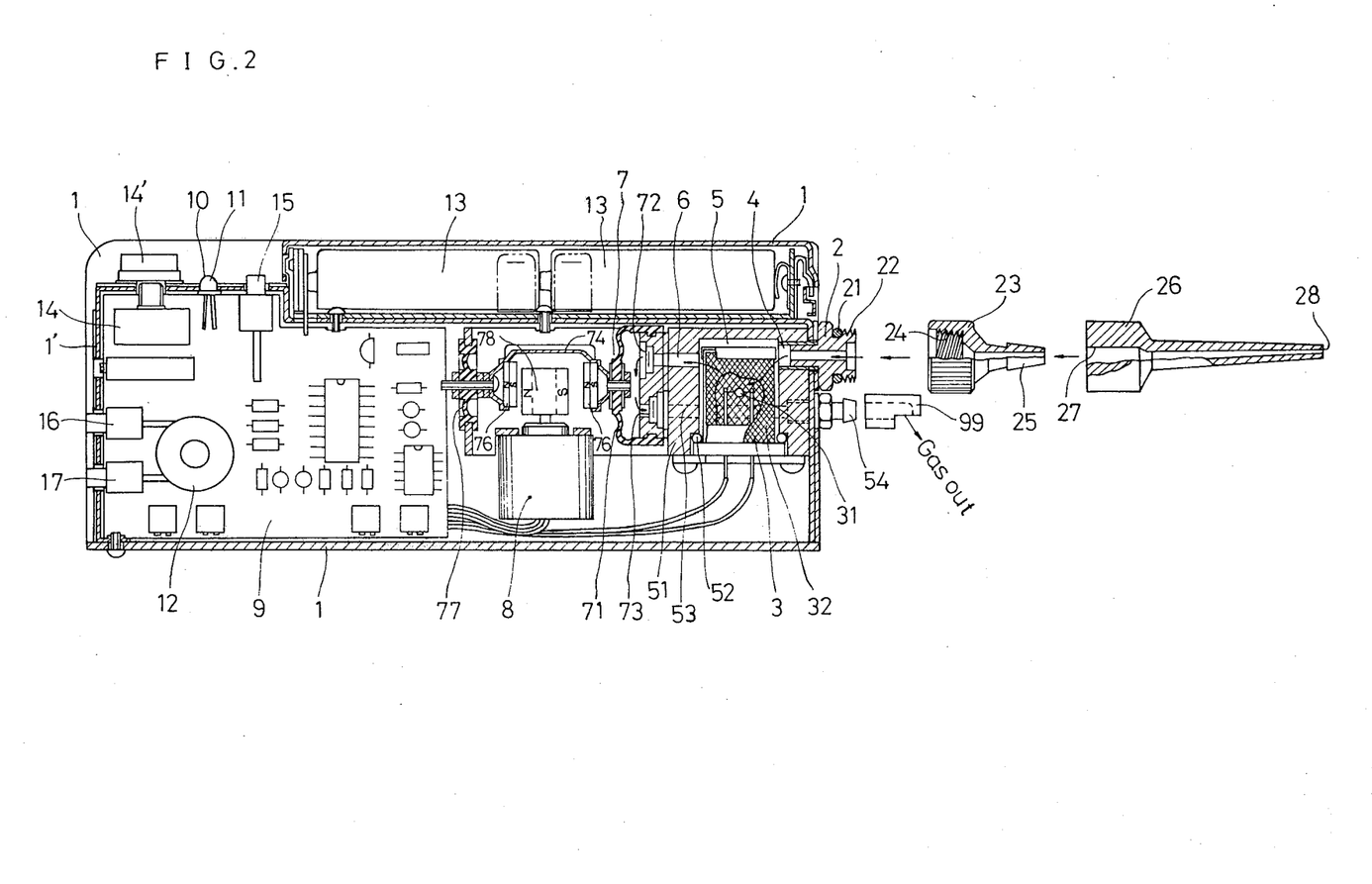
FIG. 2 is a side view with its case cover removed of the apparatus of FIG. 1, together with fragmental side view of attachments.
Figure 3:
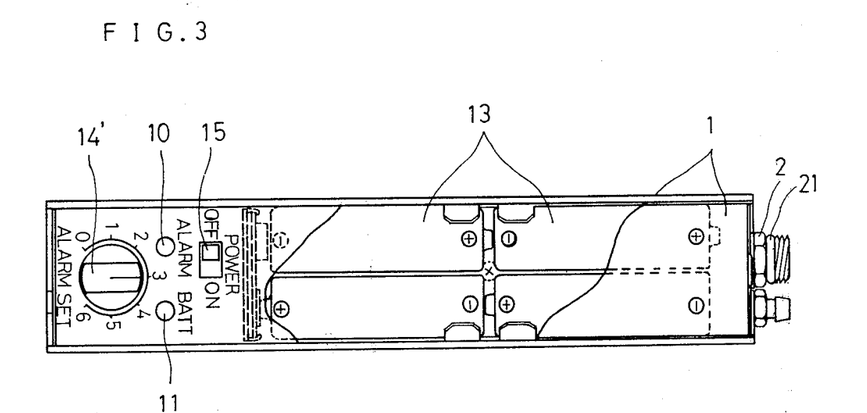
FIG. 3 is a fragmental plan view.

FIG. 1 is a perspective view showing overall appearance of the embodiment, FIG. 2 is a side view of the gas leakage detector of FIG. 1 with its case cover removed together with fragmental side view of attachments and FIG. 3 is a fragmental plan view. As shown in these figures, the apparatus has a case 1 on which a gas intake connector 2 is disposed at one end. The case contains the following components and parts:

a solid state gas sensor 3 of a known type, for example having a small block of sintered metallic oxide to be heated to a temperature of over 300° C. by electric heater of platinum wires, a gas intake path 4,5 which is connected to an input end of the gas intake connector 2, said solid state gas sensor 3 being disposed in an expanded part 5 of the gas intake path, a suction pump 7 connected to an output end 6 of the gas intake path 4,5 and driven by a small battery-driven motor 8, a printed circuit board 9 containing thereon a variable frequency oscillator which changes frequency of its output pulse responding to the input voltage from the solid state sensor, at least a lamp 10 or a small speaker 12 as an alarm indicator which is energized by a current controlled by the variable frequency oscillator, in a manner that pulsation frequency of interrupted ringing of small speaker or interrupted lighting of lamp changes responding to gas concentration measured by said gas sensor and primary or secondary batteries 13 to energize the electric circuit of the printed circuit board 9 and all the abovementioned components.

Besides the abovementioned components, a variable resistor 14 for setting detection level is fixed on the case wall 1', and a knob 14' of the variable resistor 14 is provided outside the case wall. And furthermore, a power switch 15 to switch on or off the circuit from the batteries 13, a battery check light 11, a buzzer switch 17 and a selection switch 17 for selection of operations for different kinds of gasses are provided on the case wall 1'.

For the solid state gas sensor 3, a sintered metallic oxide-coated wire type sensor having an element 31 is used, wherein a non-oxidizable metal wire such as platinum wire is coated with sintered block of metallic oxide such as $SnO_2$ and the metallic oxide block is heated to a predetermined temperature of over 300° C. by energizing with a current, thereby producing change of thermal conductivity of the metal oxide block by chemisorption of gas to be detected and consequently obtaining change of resistance of the metal wire due to change of temperature thereof which is measured by means of an electric circuit. The metallic oxide-coated wire type gas sensor has the following advantages: (1) the time from a switching-on to an achievement of stabilization of detection sensitivity is only two or three seconds, which is far shorter than several to several tens of minutes required for stabilization of a gas sensor utilizing a change of resistance of a semiconductor body per se, (2) sensitivity of the metal oxide coated wire type element is high especially for low concentration gas and for inflammable (combustible) gas, such as $CH_4$ or liquid petroleum gas or some kind of gas to be easily adsorbed, for example, $NO_2Cl_2$ or some kind of fluoroethylene, and (3) only low voltage supply is required. The metallic oxide-coated wire type gas sensor has a logarithmic concentration-voltage output characteristic. These are especially important for portable high sensitivity gas detectors wherein switching on and off are made very frequently and high sensitivity detection must be made in a short time with a quick response with a handy portable apparatus. The element 31 mounted in a net case is disposed in the expanded part 5 of the gas intake path 4,5 which is formed in a sensor mounting block 51 made of metal, to which the gas sensor 3 is mounted with an O-ring. The sensor mounting block 51 has an exhaust path 53 therethrough to an outlet piece 54 fixed on the case wall 1'.

The suction pump 7 comprises a diaphragm 71 made of synthetic rubber which is mounted on a face of the sensor mounting block 51 in a manner to cover a first port 72 leading to the output end 6 of the gas intake path 4,5 and a second port 73 leading to the exhaust path 53. The first port 72 and the second port 73 respectively comprises known pump valves. One end of a driving frame 74 comprising a pair of permanent magnets 75 and 76 is fixed to a moving top part of the diaphragm 71 and the other end of the driving frame 74 is movably held by a movable holder 77 made of, for example, flexible rubber. A cylindrical permanent magnet 78 mounted on a shaft of the motor 8 is disposed in a manner that poles of the cylindrical permanent magnet 78 face the poles of the abovementioned pair of permanent magnets 75 and 76, thereby to reciprocatingly drive the latter by attracting force and repelling force between the magnets when the cylindrical permanent magnet 78 rotates by means of the motor 8. Accordingly, when the motor 8 is driven by an electric current from batteries 13, the diaphragm 71 reciprocatingly moves, and thereby, the gas is inhaled from the intake connector 2 through the intake path 4,5 and is exhausted from the exhaust path 53, so that the gas contacts the element 31 of the gas sensor 3. A desirable capacity of the suction pump is to suck 100 to 400 cc/min. for obtaining a high detective sensitivity and a desirable response speed.

For ordinary use, a plug 23 is connected to the gas intake connector 2 by means of coupling an internal screw 24 thereof to an external screw 22 of the gas intake connector 2 with an O-ring 21 positioned at a seat of connector 2 behind threads 22 for a gas-tight coupling, and further a nozzle 26 made of a synthetic rubber and having a through-hole 27 is connected by inserting a top tube part 25 of the plug 23 in the through hole 27. The inside diameter of the through-hole in the nozzle or other long attachment should be preferably 2 to 4 mm in order to assure response speed and sensitivity.

Figure 4:
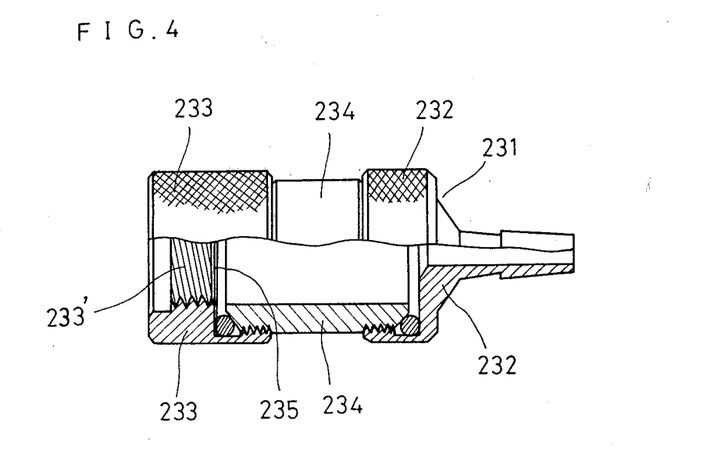
FIG. 4 is a fragmental side view of a drain filter as an attachment of the apparatus.

FIG. 4 shows a drain filter 231 to be used in place of the plug 23 when the place of gas detection has drops of water or various other liquid or muddy substance which may be harmful to the sensor 3. The drain filter 231 comprises a glass tube 234 between the top part 232 of the same shape as the plug 23 and the bottom part 233 having an internal screw 233'. Both ends of the glass tube 234 are tightly sealed to the top part 232 and the bottom part 233 with O-rings inbetween. A disposable filter 235 is mounted between the glass tube 234 and the bottom part 233 to stop drops of water, oils or muddy substance.

Figure 5A:
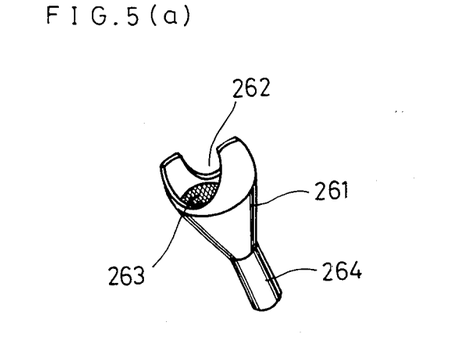
FIG. 5(a) is a perspective view of an attachment to detect gas leakage from a pipe and FIG. 5(b) is a perspective view of using the attachments of FIG. 5(a).
Figure 5B:
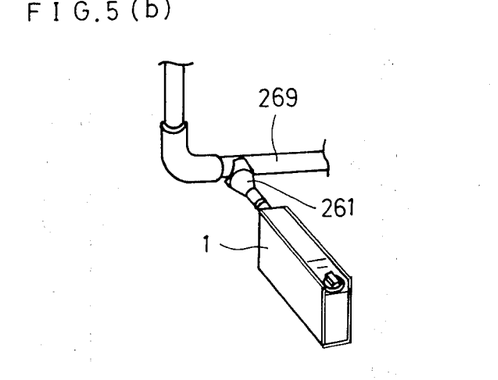

FIG. 5(a) is a perspective view of an adapter 261 to be used in place of the nozzle 26. The adapter 261 has an arc-shaped recess 262 on an expanded end for good contacting to a gas pipe 269 whose gas leakage is to be detected as shown in FIG. 5(b). The adapter 261 has a mesh filter 263 in the space of the recess 262 in order to stop inhaling of rust or any other stains of the pipe 269. The body and connecting end 264 of the adapter 261 is preferably made of synthetic rubber for good fitting to the pipe 269 as well as to the top tube part 25 of the plug 23 (of FIG. 2).

Figure 5C:
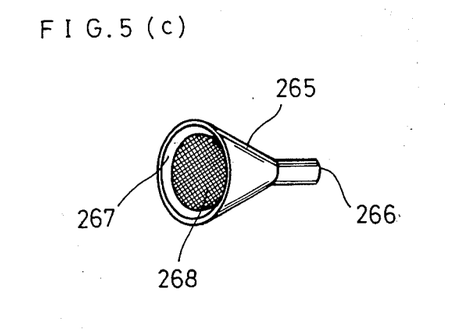
FIG. 5(c) is a perspective view of an attachment to detect gas leakage from a wall or floor.

FIG. 5(c) shows another adapter 265 for use in gas leakage detections on a wall or flow in which a gas pipe is buried. The adapter has an intake opening 267 at its expanded end, a narrow connecting end 266 on the opposite end and a mesh filter 268 near the opening 267 in the space of the expanded end. The body and the connecting end 266 of the adapter is preferably made of synthetic rubber for good fitting to the wall or floor as well as to the top tube part 25 of the plug 23.

A gas outlet cap 99 is mounted on the exhaust pipe 54 on the wall 1' in order to exhaust the gas to a desired direction.

Figure 6:
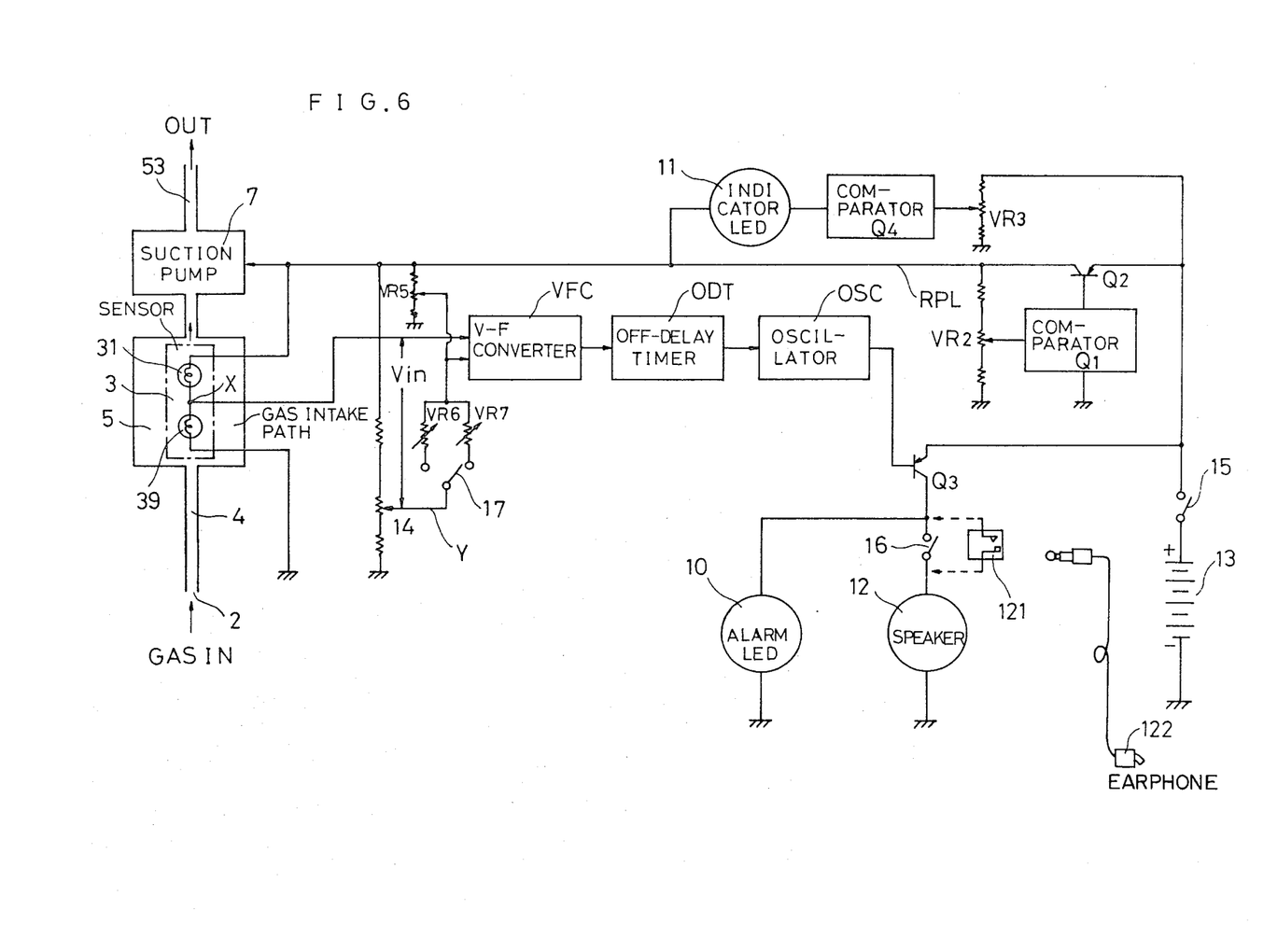
FIG. 6 is a block diagram showing electric constitution of the apparatus shown by FIGS. 1 to 4.

FIG. 6 is a block diagram of the electric circuit of the present invention main parts of which are on the printed circuit board 9.

As shown in FIG. 6, batteries 13 feed power through the power switch 15 to the circuit of an output transistor Q3, in the collector circuit of which an LED 10 as an alarm lamp is connected. Also the small speaker 12 as an alarm buzzer is connected via the buzzer switch 16 across the LED 10. If desired, an ear phone socket 121 can be connected across the contacts of the buzzer switch 16, so that the user can use an ear phone 122 in a very noisy place. The power of the batteries 13 is fed also to a transistor Q2 which constitutes known regulated power supply together with a known voltage comparator Q1 and a variable resistor VR2 for voltage setting, to feed a constant voltage to a line RPL. A semi-fixed variable resistor VR3 is connected across the positive and negative terminals of the battery 13. A second LED 11 as the battery indication lamp and a known voltage comparator circuit Q4 are connected in series across the regulated power supply line RPL and a sliding terminal of the variable resistor VR3.

The regulated power supply line RPL further feeds power to the pump 7, to the heater wires of the gas sensor 3 and to the below mentioned voltage-frequency converter (hereinafter VF converter) VFC, off-delay timer ODT and oscillator OSC. The variable resistor 14 for alarm setting and a zero adjusting variable resistor VR5 are connected across the regulated power supply line and the negative terminal of the power source. The heater wires of the gas sensor consists of the detection wire in the gas detection element 31 exposed to the gas and a reference wire, which is in a reference element 39 not exposed to the gas but connected in series to and disposed in a close proximity to the detection wire of the detection element 31, for compensating any ambient temperature influence. The junction point X between the detection wire and the reference wire is connected to a first input terminal of the VF converter VFC. Sliding terminal Y of the variable resistor 14 is connected to the moving contact of the selection switch 17. Fixed contacts of the selection switch 17 are connected respectively through semi-fixed variable resistors VR6 and VR7 for alarm range setting to a second input terminal of the VF converter VFC, and further to the sliding terminal of the variable resistor VR5. The output terminal of the VF converter VFC is connected to the input terminal of the off-delay timer ODT, and the output of the off-delay timer ODT is input to the oscillator OSC which gives the output to the base of the output transistor Q3.

Figure 7:
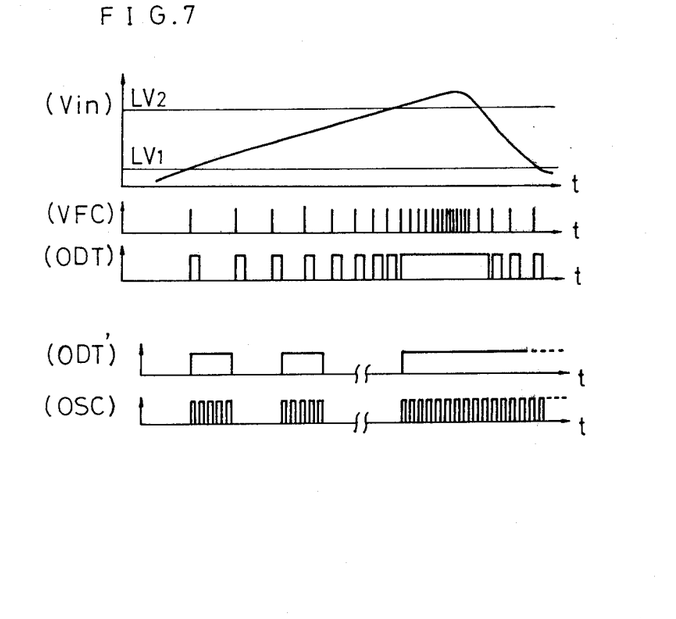
FIG. 7 is waveform chart showing waveforms of signals of various parts of the circuit of FIG. 6.

Operation of the circuit shown in FIG. 6 is elucidated now referring to the waveform chart of FIG. 7 showing signals of several parts of the block diagram of FIG. 6.

When the power switch is turned on, the battery indication lamp 11 is lit if batteries 13 show a proper terminal voltage. At the same time, the transistor Q2 feeds the voltage-regulated power to the line RPL, and hence the pump 7 works to inhale gas into the gas-intake path 5 and the platinum wire heater of the gas sensor 3 is energized to heat the element to a predetermined temperature of over 300° C.

When the combustible gas contacts the gas sensor 3, the heat conductivity of the metal oxide film on the heater wire of the gas detection element 31 becomes small, and therefore due to an increase of heat conduction the temperature of the wire is lowered, and hence the resistivity of the heater wire increases. Therefore, the potential at the junction point X is raised. A 20 mV voltage change for the gas concentration of 100 ppM of butane is obtainable. When the gas concentration increases, the input voltage difference Vin across the first and the second input terminals increases as shown in waveforms (Vin) of FIG. 7, and hence, the VF converter VFC increases its output frequency as shown by the waveform (VFC) of FIG. 7. The off-delay timer ODT produces square waves of uniform time width, which are triggered by the output pulses of the VF converter VFC. Therefore, the output wave of the ODT converter becomes continuous for values of the input voltage difference Vin above a predetermined level LV2. The oscillator OSC provides an audio frequency wave for example 1000 Hz, which is amplitude-modulated by 100% as shown by FIG. 7 (OSC) by the input signal from the off-delay timer ODT as shown by FIG. 7 (ODT'). In other words, the 1000 Hz signal is issued only in blocks of time when the output signal of the off-delay timer ODT is in "H" level. The output transistor Q3 amplifies the output signal of the oscillator OSC, and therefore, the waveform as that of FIG. 7 (OSC) is fed to the alarming LED 10 and, when the switch 16 is closed, to the speaker 12, thereby to alarm a detection of gas. Accordingly, as is shown by FIG. 7 (ODT') and (OSC), the current flowing through the LED 10 and the speaker 12 is a pulsating current which pulses ON and OFF intermittently with a pulsing frequency of, for example, 1 to 20 times per second. Therefore the light of the LED 10 and the sound of the speaker 12 pulses 1 to 20 times depending on the gas concentration. Though the light is further pulsing also at 1000 Hz, such high frequency is not noticeable by human eyes, and therefore, pulsing of 1 to 20 times per second only is observed.

Experiments show that human eyes and ears can not notice pulsing of light and sound at more than 20 times per second, and therefore the upper limit of the pulsing frequency is preferably about 20 Hz. The inventors found that for the portable gas leakage apparatus of the type of present invention whereby detection of the gas leakage of a predetermined concentration range is enough, the mode of indication is preferably simple in order to obtain reliable and quick detection. Therefore, for concentrations exceeding a predetermined high level, there is no need of gradually changing the mode (i.e., pulsing frequency) of the alarm. Therefore, it is sufficient that a highest noticeable pulsing frequency, for example 20 Hz, is set to correspond to the predetermined high level LV2 of the input voltage difference Vin of FIG. 7(Vin). That is, for the concentrations higher than such predetermined high level, it is preferable to make the alarm light and the alarm sound continuous for each handling, instead of further raising pulsing frequency in vain. In order to meet such requirement, the waveform of the control signal to be given to the input terminal of the oscillator OSC is designed in a manner that widths of pulses are uniform and spaces between the pulses only changes responding to the gas concentration. Such control signal is produced by feeding output signal of the VF converter VFC to the off-delay timer ODT and appropriately selecting the pulse width of the off-delay timer ODT, for example 25 m. sec. The off-delay timer ODT can be replaced with a known one-shot multivibrator since the former and the latter function similarly.

Inventors studied the indication of the lower limit of the concentration in view of easy handling of the apparatus, and the inventors study showed that a pulsing frequency of less than 1 Hz is not suitable for the use of the portable detector. Therefore, the lower limit of the output frequency of the VF converter VFC should preferably be set to such desired selected value. This is achieved by employing the circuit shown in FIG. 8 as the VF converter VFC.

Figure 8:
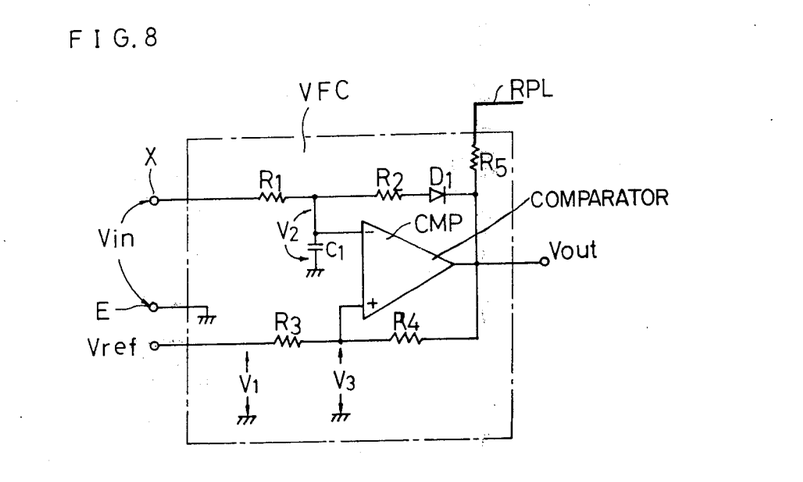
FIG. 8 is a circuit diagram of the V–F converter of FIG. 6.

The VF converter VFC shown in FIG. 8 comprises a comparator CMP whose output terminal Vout is the output terminal of the VF converter VFC. The input voltage difference signal Vin is impressed across an input terminal X and a ground and the earth terminal E. A resistor R1 is connected between the input terminal X and the negative input terminal "−" of the comparator CMP, and a resistor R2 and a diode D are connected in series between the negative input terminal "−" and the output terminal Vout, which is connected through a resistor R5 to the positive power supply line RPL. A capacitor C1 is connected between the negative input terminal "−" and the ground E. A resistor R4 is connected between the output terminal Vout and the positive input terminal "+" of the comparator CMP, and a resistor R3 is connected between the positive input terminal "+" and a reference input terminal Vref to which a predetermined reference voltage V1 is impressed. The resistors R3 and R4 are for positive feedback.

Operation of the VF converter of FIG. 3 is as follows:

At first, the capacitor C1 is charged to the voltage of Vin through the resistor R1.

When the input voltage Vin is lower than the voltage V3, the output terminal Vout is in "H" level.

As the gas concentration increases and hence the input voltage Vin increases thereby charging the capacitor C1, the potential at the negative input terminal "−" becomes higher than the potential at the positive input terminal "+". Then the comparator CMP becomes OFF and the output terminal Vout comes to "L" level, and accordingly the charge of the capacitor C1 is discharged through the resistor R2 and the diode D1 at a rate of the time constant C1·R2. By this discharging, the voltage V3 is reduced from V3a to V3b in the waveform chart of FIG. 9 (Vin) which shows input voltage Vin.

Figure 9:
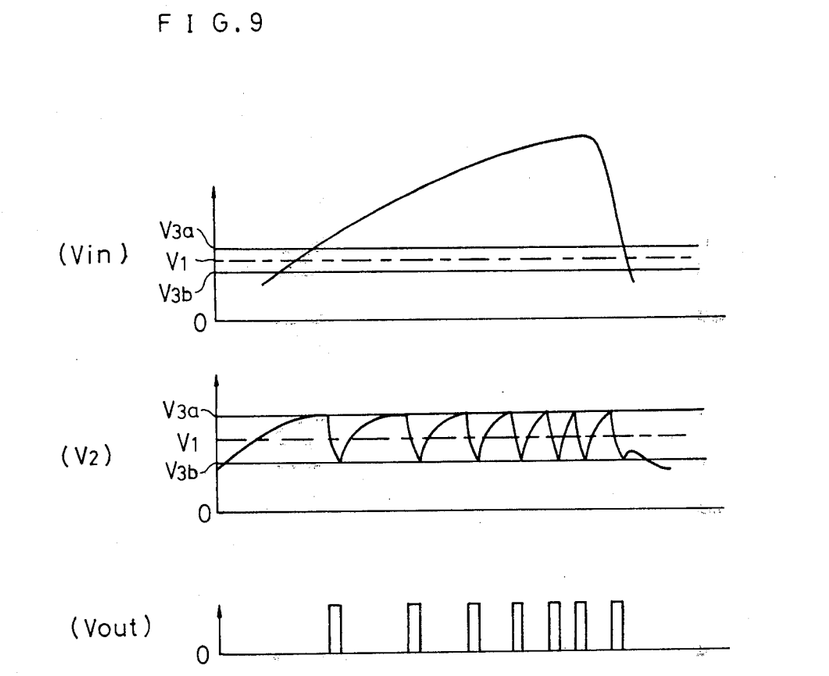
FIG. 9 is a waveform chart showing waveforms of various parts of the circuit of FIG. 6.

When the voltage of the capacitor C1 discharges to the level of V3b, the comparator CMP restores to the OFF state, making the output terminal Vout in "H" level, thereby the voltage V3 goes back from V3b to V3a of FIG. 9(Vin), and the capacitor C1 is again begins to charge through the resistor R1, (namely, charging occurs with the time constant of C1·R1). The relation between the timer constants are selected to be:

C1·R2 << C1·R1.

When the input voltage Vin becomes high again, the charging time becomes shorter than the case with the lower Vin voltage as shown by FIG. 9, (Vin) and (V2), and therefore, the time from an OFF of the comparator CMP to the subsequent ON thereof becomes short, that is, the "L" periods of the output terminal Vout becomes short, while the discharging time period defined by the C1·R2 time constant is retained unchanged. This means that the signal at the output terminal Vout becomes as shown by FIG. 9(Vout).

In the circuit of FIG. 8, by suitably selecting hysteresis gap V3a−V3b of the comparator CMP, which is determined by the resistances of the resistors R3 and R4, the longest period of the abovementioned operation of the circuit can be selected to be a desired value, for example, 1 second. In one example, the condition for obtaining the longest period of 1 second is as follows: hysteresis gap (V3a−V3b) is about 80 mV and V3a−V1 ≈ 40 mV = V1−V3b, where CMP is LM339 made by Intersil Inc. of U.S.A., R1 = 47 kΩ, R2 = 4.7 kΩ,
R3 = 10 kΩ,
R4 = 220 kΩ,
R5 = 4.7 kΩ,
C1 = 1 μF and
Voltage between RPL and the ground: 5 V.

The circuit of FIG. 8 has a particularly advantageous feature. By employing the comparator CMP as the active element, the change of the "L" period is equally obtainable either by changing the input signal level Vin or by changing the reference voltage Vref which is the potential of the sliding terminal Y of the variable resistor 14 in FIG. 6. Accordingly, the sliding terminal Y of the variable resistor 14 is usable to set the level of the gas concentration, for example, 50 ppm, where alarm signal with the lowest pulsing frequency, for example 1 Hz, is to be issued. Such adjustment is necessary to attain detection of the gas leakage with as high sensitivity as possible in relation to the level of background contamination of the atmosphere.

The abovementioned circuit of FIG. 8 is made with a small number of components and still is very advantageous.

Actual use of the apparatus for obtaining the possible highest sensitivity of detection is made as follows:

After a lapse of 3 to 4 seconds from switching on of the power switch 15 for stabilization of the detection sensor 3, by handling the knob 14' of the variable resistor 14, its sliding terminal Y is once turned to its very low position, so that the VF converter VFC ceases its output signal. Thereafter, the knob of the variable resistor 14 is carefully adjusted to raise its sliding terminal Y, and find a critical position where the VF converter to start issuing pulsating output signal of a lowest frequency, for example 1 Hz. Then from the critical position, the position of the sliding terminal Y is again lowered by a predetermined very narrow one unit, where the VF converter VFC does not issue the pulse signal. With the abovementioned procedure, the apparatus is now adjusted at a very sensitive waiting condition to detect the gas leakage. For different gases, for example, manufactured gas and natural gas, the range of the detection is considerably different. Therefore, in order to obtain high sensitive detection with similar position of the sliding terminal Y of the variable resistor 14 for both gases, the detection range is switched by use of the switch 17 to select a series resistor VR6 or VR7 to be connected between the point Y and the input terminal of the VF converter VFC.

Figure 10:
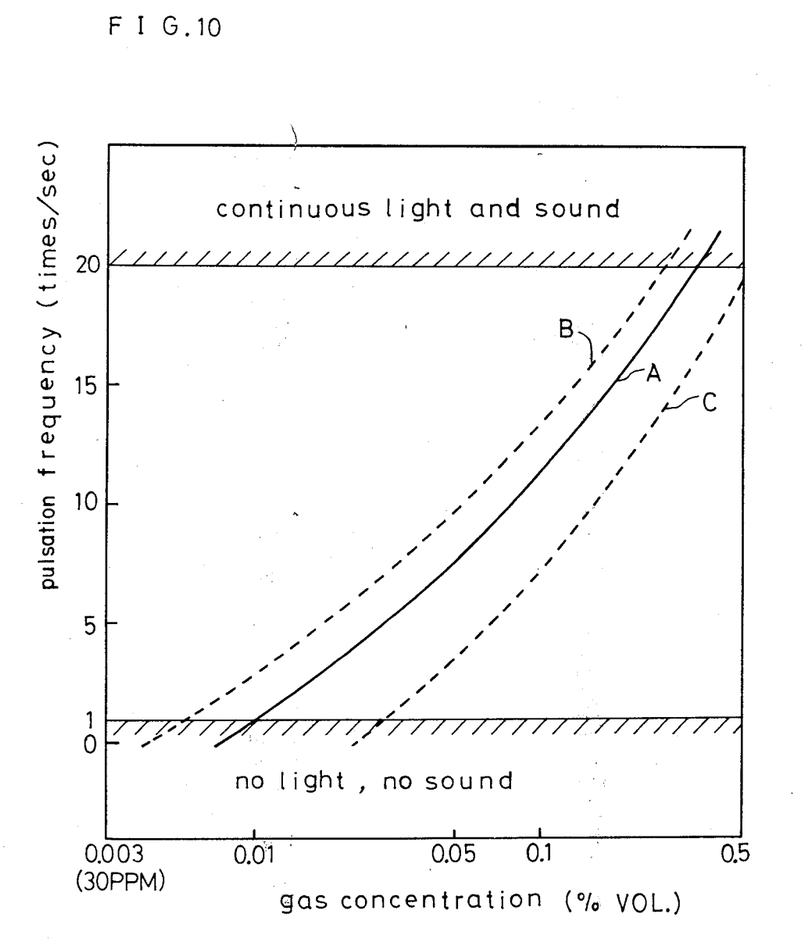
FIG. 10 is a graph showing an example of relation of gas concentration and blinking frequency of the alarm light and sound.

FIG. 10 shows an overall characteristic curve of one example of the apparatus. The curve shows the case when the alarm set knob is suitably adjusted. As shown by the graph, the apparatus has a good logarithmic characteristic with respect to the concentration, which implies applicability for very wide range of concentration of gas. In the upper area of the pulsing frequencies above 20 Hz which is for the concentration value of above 0.35 volume %, the light and sound alarm signals are made continuous. In the lower area of the pulsing frequencies below 1 Hz which is for the concentration value of about 0.01 volume %, the light and sound alarm signals are stopped.

As the sliding terminal Y of the variable resistor 14 is slid upwards or downwards, the curve A of FIG. 10 shifts rightwards, for example, to the curve C or leftwards, for example, to the curve B. By carefully sliding down the sliding terminal Y from the abovementioned critical position, thereby shifting the curve leftwards to a very high sensitive position, when the ambient atmosphere is very clean, such a small leakage of about 50 ppm or lower can be reliably detected.

The gas intake rate in the intake path is preferably slow for the sake of high sensitivity detection in case of small leakage amount. However, the intake rate should not be too small in order not to lose quick response characteristic of the apparatus of the present invention.

Provided that all of the leakage gas can be taken in the gas intake path, which inhales the air at the rate of 200 cc/min, and provided that the leakage rate of the gas is $3.3 \times 10^{-4}$ cc/sec, then the concentration of the gas in the gas intake path is 100 ppm, which is sufficiently within the stably detectable range of the apparatus. This means that the apparatus of the present invention can detect with higher sensitivity than the conventional method utilizing a detection liquid, maximum sensitivity of which method is about $5 \times 10^{-4}$ cc/sec.

If the circumstances (for example, ambient atmosphere) permit, the detectable lowest concentration is $1.6 \times 10^{-4}$ atom cc/sec which corresponds to the concentration of 50 ppm.

In view of hydrodynamic resistance, the gas intake path and the attachment should have the inside diameter of 3 mm or larger; and for the inner diameter of 3 mm, the inhaling rate of the pump 7 should be about 200 cc/min, in order to assure reasonable response speed of about 2 seconds for an extended attachment having about 1 m length. A usable range of the inhaling rate of the suction pump 7 is 100 to 400 cc/min in order to obtain good result. The usable range of average inside diameter of tubular parts of the attachment and the gas-intake path is between 2 to 4 mm. When the inhaling rate of the pump 7 is over 400 cc/min or the inside diameter is below 2 mm, the gas flow speed becomes too fast thereby causing a dilution of the intaken gas in the apparatus thereby decreasing the detection sensitivity. When the inhaling rate is under 100 cc/min or the inside diameter is over 4 mm, the detection response speed becomes too slow for this kind of apparatus.

What is claimed is:

1. A gas leakage detector comprising:
    a solid state gas sensor having a sintered metallic oxide block which changes its thermal conductivity with chemical adsorption thereto and a wire for transforming changes of thermal conductivity into a gas sensor electrical signal,
    a gas intake path for conducting gas to said gas sensor,
    a suction pump for drawing gas through the intake path to said gas sensor,
    a voltage-frequency converter (VFC) for providing a pulse output frequency that is a function of the gas sensor electrical signal, and
    an alarm indicator including sound and/or light controlled to pulsate in response to said VFC,
    wherein the sound and/or light of said alarm indicator is controlled to pulse in a manner that the frequency of pulsation changes between a predetermined lower limit which corresponds to a lower limit of concentration of gas to be detected and a predetermined higher limit which corresponds to a higher level of concentration of gas to be detected, the time duration of each pulsation of light and/or sound being uniform regardless of any change of pulsation frequency, the light and sound being continuous at said higher limit.

2. A gas leakage detector in accordance with claim 1, wherein said lower limit is substantially 1 Hz and said higher limit is substantially 20 Hz.

3. A gas leakage detector in accordance with claim 1 further comprising controlling means including an off-delay timer or a one-shot multivibrator which controls an output signal of an audio frequency oscillator to produce pulsating sound signal.

4. A gas leakage detector in accordance with claim 3, wherein said off-delay timer or one-shot multivibrator produces a pulse train wherein an on-period of each pulse being about 25 m sec.

5. A gas leakage detector in accordance with claim 1, wherein said voltage-frequency converter comprises a first input terminal which receives said gas sensor electrical signal and a second input terminal which receives a reference voltage from a variable voltage source comprising a variable resistor to adjust said reference voltage, said variable resistor being for adjusting a level of detection.

6. A gas leakage detector in accordance with claim 5, wherein said voltage-frequency converter includes a comparator comprising
    an input terminal connected by a first resistor to said first input terminal of said voltage-frequency converter, by a capacitor to the grounded terminal of a power source and by a series connection of a second resistor and a diode to its output terminal and,
    another input terminal connected by a third resistor to said second input terminal of said voltage-frequency converter and by a fourth resistor to said output terminal, which is connected through a fifth resistor to another terminal of said power source.

7. A gas leakage detector in accordance with claim 5, which further comprises a range switching circuit for selecting detection ranges for different types of gases connected between said second input terminal and said variable voltage source, said range switching circuit comprising a change-over switch and plural semi-variable resistors connected thereto.

8. A gas leakage detector in accordance with claim 1, wherein a series connection of a sound alarm indicator and a switch is connected in parallel to a light alarm indicator.

9. A gas leakage detector in accordance with claim 1, wherein said suction pump comprises
    a battery-driven motor,
    a rotatable permanent magnet fixed on a shaft of said battery-driven motor,
    a pair of permanent magnets disposed on both sides of said rotatable permanent magnet and fixed on a reciprocatingly movable frame,
    a diaphragm covering a closed space therewith and connected at its movable part to said reciprocatingly movable frame, and
    a pair of valves mounted on a first port which is in said closed space and leading to said gas intake path and on a second port which is in said closed space and leading to an exhaust path.

10. A gas leakage detector in accordance with claim 1, wherein an inhale rate of said suction pump is 100 to 400 cc/min, and average inside diameter of lengthy tubular part of said gas intake path is 2-4 mm.

11. A gas leakage detector in accordance with claim 1, which further comprises an attachment to be disconnectably connected to a gas intake connector which is disposed on a case wall and leading to said gas intake path, inside diameter of said attachment being 2-4 mm.

12. A gas leakage detector in accordance with claim 11, wherein said attachment has a short tubular body of transparent or translucent material and a fine filter at its down stream end part.

13. A gas leakage detector in accordance with claim 11, wherein said attachment has an elongated nozzle.

14. A gas leakage detector in accordance with claim 11, wherein said attachment has an extended end part having an arc-shaped recess to fit side of a tubular matter.

15. A gas leakage detector in accordance with claim 14, wherein said end part has a mesh.

16. A gas leakage detector in accordance with claim 11, wherein said attachment has a conical extended end part having flat opening to fit a flat matter.

17. A gas leakage detector in accordance with claim 16, wherein said end part has a mesh.

18. A gas leakage detector comprising:
 a solid state gas sensor having a sintered metallic oxide block which changes its thermal conductivity with chemical adsorption thereto and a wire for transforming changes of thermal conductivity into a gas sensor electrical signal,
 a gas leakage path for conducting gas to said gas sensor,
 a suction pump for drawing gas through the intake path to said gas sensor,
 a voltage-frequency converter (VFC) for providing an output pulse frequency that is a function of the gas sensor electrical signal,
 an off-delay timer (ODT) or a one shot multivibrator for providing a signal responsive to the output of the VFC, and
 an alarm indicator including sound and/or light controlled to pulsate in response to an output of the ODT or multivibrator,
 the pulsation frequency changing between a predetermined lower limit corresponding to a lower limit of concentration of gas to be detected and a predetermined higher limit corresponding to a higher level of concentration of gas to be detected, the time durations of each pulsation of light and sound being uniform regardless of any change of pulsation frequency, the light and sound being continuous at said higher limit.

19. A gas leakage detector according to claim 18, wherein said lower limit is substantially 1 Hz and said higher limit is substantially 20 Hz.

20. A gas leakage detector according to claim 18, wherein said off-delay timer or one-shot multivibrator produces a pulse train wherein an on-period of each time pulse being about 25 msec.

21. A gas leakage detector according to claim 18, wherein said voltage-frequency converter comprises a first input terminal which receives said gas sensor electrical signal and a second input terminal which receives a reference voltage from a variable voltage source comprising a variable resistor to adjust said reference voltage, said variable resistor being for adjusting a level of detection.

22. A gas leakage detector according to claim 21, wherein said voltage-frequency coverter includes a comparator comprising an input terminal connected by a first resistor to said first input terminal of said voltage-frequency converter, by a capacitor to the grounded terminal of a power source, and by a series connection of a second resistor and a diode to its output terminal, and
 another input terminal connected by a third resistor to said second input terminal of said voltage-frequency converter, by a capacitor to the gounded terminal of a power source, and by a series connection of a second resistor and a diode to its output terminal, and
 another input terminal connected by a third resistor to said second input terminal of said voltage-frequency converter and by a fourth resistor to said output terminal, which is connected through a fifth resistor to another terminal of said power source.

23. A gas leakage detector according to claim 21, which further comprises a range switching circuit for selecting detection ranges for different types of gases connected between said second input terminal and said variable voltage source, said range switching circuit comprising a change-over switch and plural semi-variable resistors connected thereto.

24. A gas leakage detector according to claim 18, wherein a series connection of a sound alarm indicator and a switch is connected in parallel to a light alarm indicator.

25. A gas leakage detector according to claim 18, wherein said suction pump comprises
 a battery-driven motor,
 a rotatable permanent magnet fixed on a shaft of said battery-driven motor,
 a pair of permanent magnets disposed on both sides of said rotatable permanent magnet and fixed on a reciprocatingly movable frame,
 a diaphragm covering a closed space therewith and connected at its movable part to said reciprocatingly movable frame, and
 a pair of valves mounted on a first port which is in said closed space and leading to said gas intake path and on a second port which is in said closed space and leading to an exhaust path.

26. A gas leakage detector according to claim 18, wherein inhale rate of said suction pump is 100 to 400 cc/min, and average inside diameter of lengthy tubular part of said gas intake path is 2-4 mm.

27. A gas leakage detector according to claim 18, further comprising an attachment to be disconnectably connected to a gas intake connector which is disposed on a case wall and leading to said gas intake path, inside diameter of said attachment being 2-4 mm.

28. A gas leakage detector according to claim 27, wherein said attachment has an elongated nozzle.

29. A gas leakage detector according to claim 27, wherein said attachment has an extended end part having an arc-shaped recess to fit side of a tubular matter.

30. A gas leakage detector according to claim 27, wherein said attachment has a conical extended end part having flat opening to fit a flat matter.

31. A gas leakage detector according to claim 29 or 30, wherein said end part has a mesh.

32. A gas leakage detector according to claim 27, wherein said attachment has a short tubular body of transparent or translucent material and a fine filter at its downstream end part.

* * * * *